(12) United States Patent
Fontaine et al.

(10) Patent No.: US 7,292,333 B2
(45) Date of Patent: Nov. 6, 2007

(54) OPTICAL INTERROGATION SYSTEM AND METHOD FOR 2-D SENSOR ARRAYS

(75) Inventors: Norman H. Fontaine, Painted Post, NY (US); Eric J. Mozdy, Elmira, NY (US); Po Ki Yuen, Corning, NY (US)

(73) Assignee: Corning Incorporated, Corning, NY (US)

( * ) Notice: Subject to any disclaimer, the term of this patent is extended or adjusted under 35 U.S.C. 154(b) by 199 days.

(21) Appl. No.: 11/100,199

(22) Filed: Apr. 5, 2005

(65) Prior Publication Data

US 2005/0236554 A1    Oct. 27, 2005

Related U.S. Application Data

(63) Continuation-in-part of application No. 11/019,439, filed on Dec. 21, 2004, which is a continuation-in-part of application No. 10/602,304, filed on Jun. 24, 2003, now Pat. No. 7,057,720.

(51) Int. Cl.
*G01J 3/00* (2006.01)
(52) U.S. Cl. ..................................................... 356/300
(58) Field of Classification Search ............... 356/300, 356/445
See application file for complete search history.

(56) References Cited

U.S. PATENT DOCUMENTS

| | | | |
|---|---|---|---|
| 4,815,843 A | 3/1989 | Tiefenthaler et al. | ........ 356/128 |
| 5,479,260 A | 12/1995 | Fattinger | ..................... 356/361 |
| 6,100,991 A | 8/2000 | Challener | .................... 356/445 |
| 6,346,376 B1 | 2/2002 | Sigrist et al. | .................. 435/5 |
| 6,429,022 B1 | 8/2002 | Kunz et al. | .................. 436/164 |
| 6,570,657 B1 * | 5/2003 | Hoppe et al. | ............... 356/445 |
| 6,686,582 B1 | 2/2004 | Völcker et al. | ............... 250/216 |
| 6,785,433 B2 | 8/2004 | Tiefenthaler | ................. 385/12 |
| 7,151,598 B2 * | 12/2006 | Poponin | ..................... 356/301 |
| 2001/0021026 A1 | 9/2001 | Liu | ............................. 356/601 |
| 2001/0026943 A1 | 10/2001 | Dickopf et al. | ............. 436/164 |
| 2001/0046050 A1 * | 11/2001 | Hoyt | ........................... 356/417 |
| 2002/0001085 A1 | 1/2002 | Dickopf et al. | ............. 356/445 |
| 2002/0127565 A1 | 9/2002 | Cunningham et al. | .......... 435/6 |
| 2002/0168295 A1 | 11/2002 | Cunningham et al. | ... 422/82.05 |
| 2003/0017580 A1 | 1/2003 | Cunningham et al. | ... 435/287.2 |

(Continued)

FOREIGN PATENT DOCUMENTS

EP    1 271 219    9/2005

(Continued)

OTHER PUBLICATIONS

Tiefenthaler et al., "Integrated Optical Switches And Gas Sensors", Optics Letters, Apr. 1984, vol. 10, No. 4, pp. 137-139.

(Continued)

*Primary Examiner*—Gregory J. Toatley, Jr.
*Assistant Examiner*—Kara E. Geisel
(74) *Attorney, Agent, or Firm*—William J. Tucker; Thomas R. Beall

(57) ABSTRACT

An optical interrogation system and method are described herein that can interrogate a two-dimensional (2D) array of optical sensors (e.g., grating coupled waveguide sensors) located in a 2D specimen plate (e.g., microplate).

36 Claims, 5 Drawing Sheets

U.S. PATENT DOCUMENTS

| | | | |
|---|---|---|---|
| 2003/0017581 A1 | 1/2003 | Li et al. ................ | 435/287.2 |
| 2003/0026891 A1 | 2/2003 | Qiu et al. ................ | 427/58 |
| 2003/0027327 A1 | 2/2003 | Cunningham et al. ... | 435/287.2 |
| 2003/0027328 A1 | 2/2003 | Cunningham et al. ... | 435/287.2 |
| 2003/0031596 A1* | 2/2003 | Tanaami ................ | 422/82.08 |
| 2003/0032039 A1 | 2/2003 | Cunningham et al. ........ | 435/6 |
| 2003/0059855 A1 | 3/2003 | Cunningham et al. ....... | 435/7.9 |
| 2003/0068657 A1 | 4/2003 | Lin et al. .................... | 435/7.9 |
| 2003/0077660 A1 | 4/2003 | Pien et al. .................. | 435/7.1 |
| 2003/0092075 A1 | 5/2003 | Pepper ...................... | 435/7.9 |
| 2003/0096322 A1* | 5/2003 | Giuliano et al. ........... | 435/7.21 |
| 2003/0113766 A1 | 6/2003 | Pepper et al. ............... | 435/6 |
| 2003/0210469 A1* | 11/2003 | Boege ........................ | 359/642 |
| 2004/0132172 A1 | 7/2004 | Cunningham et al. ... | 435/287.2 |
| 2004/0132214 A1 | 7/2004 | Lin et al. .................... | 436/518 |
| 2004/0151626 A1 | 8/2004 | Cunningham et al. ........ | 422/58 |
| 2004/0223881 A1 | 11/2004 | Cunningham et al. ... | 422/82.05 |
| 2004/0266841 A1 | 12/2004 | Lange et al. ................ | 514/365 |
| 2006/0072113 A1* | 4/2006 | Ran et al. ................... | 356/445 |

FOREIGN PATENT DOCUMENTS

WO      WO 90/09560      8/1990

OTHER PUBLICATIONS

Bier et al., Real-Time Measurement of Nucleic-Acid Hybridization Using Evanescent-Wave Sensors: Steps Towards The Genosensor' Sensors and Actuators B, vols. 38-39, 1997, pp. 78-82.

Challener et al., "A Multilayer Grating-Based Evanescent Wave Sensing Technique", Sensors and Actuators B, vol. 71, 2000, pp. 42-46.

Horvath et al., "Demonstration of Reverse Symmetry Waveguide Sensing In Aqueous Solutions", Applied Physics Letters, vol. 81, No. 12 Sep. 16, 2002, pp. 4166-2168.

Brandenburg et al., "Grating Couplers as Chemical Sensors: A New Optical Configuration", Sensors and Actuators B, vol. 17, 1993, pp. 35-40.

U.S. Appl. No. 10/993,565, filed Nov. 18, 2004, Fontaine et al.
U.S. Appl. No. 11/019,439, filed Dec. 21, 2004, Caracci et al.
U.S. Appl. No. 11/027,509, filed Dec. 29, 2004, Caracci et al.

* cited by examiner

OPTICAL INTERROGATION SYSTEM AND METHOD FOR 2-D SENSOR ARRAYS

CROSS REFERENCE TO RELATED APPLICATIONS

This application is a continuation-in-part application of U.S. patent application Ser. No. 11/019,439, filed Dec. 21, 2004, which is a continuation-in-part application of U.S. patent application Ser. No. 10/602,304, filed Jun. 24, 2003, now U.S. Pat. No. 7,057,720. The contents of both patent applications are incorporated by reference herein.

BACKGROUND OF THE INVENTION

1. Field of the Invention

The present invention relates to an optical interrogation system and method capable of interrogating a two-dimensional (2D) array of optical sensors (e.g., grating coupled waveguide sensors) located for example in a microplate.

2. Description of Related Art

Today there is considerable interest in developing two-dimensional (2-D) optical sensor arrays and interrogation systems to enable Label Independent Detection (LID) of binding events, kinetic binding rates, and mass transports (cell-based assays) in a standard microplate format. These sensor arrays and measurement systems can be used to measure analyte-ligand binding events and rates (e. g. through biochemical interactions) and cellular mass transport (e.g. cell-based assays). The advantage of the standard microplate format is that it allows existing automated High Throughput Screening (HTS) and manual fluid handling systems to be used in conjunction with the sensors.

One type of label-independent interrogation system that can be used to detect binding events, kinetics, and mass transports using optical sensors (e.g., surface grating sensors) is known as an angular interrogation system. The angular interrogation system essentially monitors the output angle (or spatial shape) of light interacting with any particular optical sensor in order to determine the state of the sensor and thereby characterize any biochemical activity on the sensor's surface.

In order to accomplish this function, the angular interrogation system uses a narrowband spectral source such as a laser to emit a light beam which subsequently impinges upon the optical sensor. The optics of a launch arm tailor the optical characteristics (e.g., angular content, beam size, etc.) of this laser beam. Two mechanisms for directing the laser beam to the optical sensor in an angular interrogation system are: (1) scanning the incident angle of a collimated beam at the optical sensor; or (2) focusing a range of angles onto the optical sensor. In both cases, the goal is to determine the angular location and/or the angular shape of the sensor's resonant response and/or to detect changes in that resonant response. Toward this end, the angular interrogation system also has a receiver system that receives the optical response from the optical sensor and directs that response onto an optical detector.

If the optical detector of the angular system is placed some distance from the optical sensor, the angular shift and shape changes of the resonant response can be observed as a positional shift and change in the intensity of the received light across the plane of the optical detector. A computer can then process the measured response and algorithms can be used to characterize that response, thus enabling the detection of changes in the angle and shape of the resonant response from the optical sensor. In the case of surface sensors (e.g., surface waveguide grating sensors) the angular response provides sensitive information on a surface binding event, binding rate, and near surface mass transport.

The typical label-independent angular interrogation system is generally used to interrogate an array of optical sensors and not just one optical sensor as described above. Following are several patents, patent applications and publications that describe different types of angular interrogation systems which can be used to measure the angular responses from arrays of optical sensors.

1) U.S. Pat. No. 5,479,260, "Optical Process and Apparatus for Analysis of Substances on Sensor Surfaces," C. Fattinger, Dec. 26, 1995.
2) U.S. Pat. No. 6,100,991, "Near Normal Incidence Optical Assaying Method and System having Wavelength and Angle Sensitivity," Challener et al., Aug. 8, 2000.
3) "Grating couplers as chemical sensors: a new optical configuration," A. Brandenburg and A. Gombert, Sensors and Actuators B, 17 (1993) 35-40.
4) "Real-time Measurement of Nucleic-acids Hybridization Using Evanescent-wave Sensors: Steps Towards the Genosensor," F. Bier et al., Sensors and Actuators B 38-39, (1997) 78-82.
5) "A multilayer grating-based evanescent wave sensing technique," W. A. Challener, et al., Sensors and Actuators B 71 (2000) 42-46
6) "Demonstration of Reverse Symmetry Waveguide Sensing in Aqueous Solutions," R. Horvath et al., App. Phys. Lett., Vol 81, No 12, 16 Sep. 2002, pp 2166-2168
7) U.S. Pat. No. 6,346,376, "Optical Sensor Unit and Procedure for the Ultra-sensitive Detection of Chemical of Biochemical Analytes," H. Sigrist et al., Feb. 12, 2002.
8) U.S. Pat. No. 6,429,022 B1, "Integrated-optical Sensor and Method for Integrated-optically Sensing Substance," R. Kunz et al., Aug. 6, 2002.
9) U.S. Patent Application No. 2001/0026943 A1, "SPR Sensor System," S. Dickopf et. al., Oct. 4, 2001.
10) U.S. Patent Application No. 2002/00001085 A1, "Set-up for Measuring Instruments for the Parallel Readout of SPR Sensors," S. Dickopf et. al., Jan. 3, 2002.

The contents of these documents are incorporated by reference herein.

Unfortunately, these traditional angular interrogation systems all suffer from one or more drawbacks. For instance, the traditional angular interrogation systems that scan or re-position the optical sensors or that move or switch critical optical components (such as the laser source) suffer from measurement errors due to errors in the motion and repeatability of positioning these critical components (see document nos. 6 and 7). The ensuing measurement errors due to the movement can then dominate the level of achievable measurement sensitivity. Furthermore, the act of scanning the angle or of moving, switching, or precisely re-positioning these critical components decreases the maximum array interrogation speed that is achievable by such angular interrogation systems.

In addition, some traditional angular interrogation systems use array size reduction or image reduction methods to direct optical responses from two dimensional arrays of optical sensors onto small area detectors (see document nos. 8 and 9). However, these types of traditional angular interrogation systems have resorted to scanning of the angle (or wavelength) to trace the sensor responses for the entire sensor array and as such they have problematic dynamic range, scanning speed, and/or scanning repeatability issues.

In fact, all traditional angular interrogation systems described to date must sacrifice one or more desirable attributes in order to achieve a high angular measurement sensitivity or a high 2-D array detection speed. Accordingly, there has been a need for an angular interrogation system that can address these shortcomings and other shortcomings of the traditional angular interrogation systems. These needs and other needs are satisfied by the angular interrogation system and method of the present invention.

BRIEF DESCRIPTION OF THE INVENTION

The present invention includes an optical interrogation system and method that can interrogate a two-dimensional (2D) array of optical sensors (e.g., grating coupled waveguide sensors) located in a 2D specimen plate (e.g., microplate). In one embodiment, the optical interrogation system has a launch system which directs an array of light beams towards the array of sensors in the two-dimensional specimen plate. The optical interrogation system also has a receive system that includes a Keplerian beam expander (used in reverse as a beam condenser) which receives an array of light beams reflected from the array of sensors and directs each received light beam to a unique region on the detection plane of a small area detector (e.g., CCD camera). In addition, the optical interrogation system has a processor that analyzes changes in the position or shape of each detected light beam to determine if a binding event (biochemical interaction) or a mass transport (cell-based assay) occurred, or to determine the rate of binding (kinetics) that occurred on each sensor.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Referring to FIGS. 1-7, there are disclosed in accordance with the present invention an optical interrogation system that can be used to interrogate specimens on an array of sensors that are located for example in a microplate. It should be readily appreciated by those skilled in the art that the optical interrogation system can be used to interrogate a specimen array to determine whether or not a biological substance such as a cell, molecule, protein, drug, chemical compound, nucleic acid, peptide or carbohydrate is present within any one of the specimens in the specimen array. The optical interrogation system can also be used to perform other label or label-free studies such as photoluminescence assays, fluorescence assays, scattering assays, absorbance assays, cell migration assays, drug permeability assays, drug solubility studies, virus detection studies and protein secretion studies. Accordingly, the optical interrogation system described herein should not be construed in a limited manner.

Figure 1:
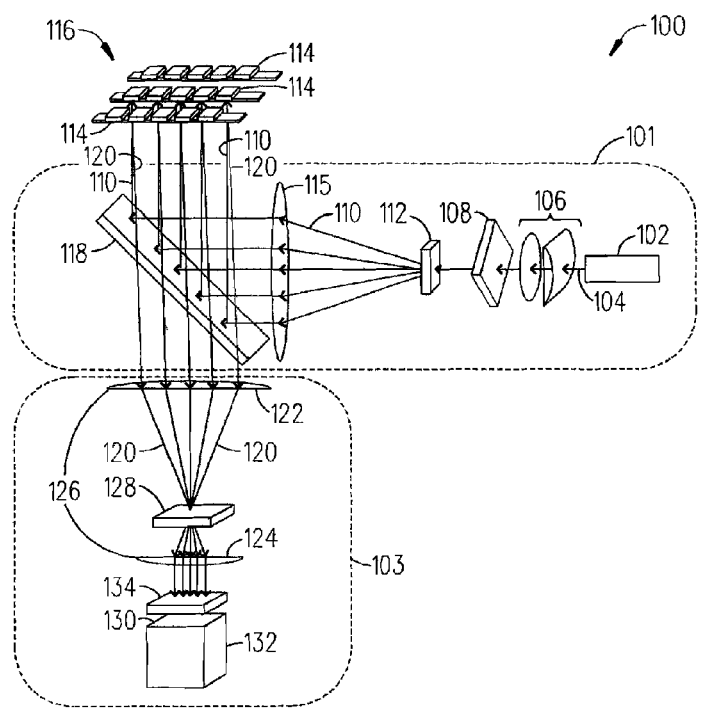
FIG. 1 is a block diagram of an optical interrogation system in accordance with one embodiment of the present invention.

Referring to FIG. 1, there is shown a block diagram of an optical interrogation system 100 in accordance with one embodiment of the present invention. As shown, the optical interrogation system 100 includes a launch system 101 and a receive system 103. The launch system 101 has a light source 102 (e.g., laser 102) which emits a light beam 104 that is passed through beamlet conditioning lens(es) 106 (discussed below) and a polarizor 108 and then is divided into a 2-dimensional array of beamlets 110 by a diffractive optic 112 (e.g., 7×7 diffractive optic 112). The central propagation axes of these beamlets 110 (black arrows) are made parallel and equidistant on a grid-spacing of 9 mm×9 mm (for example) by an auto-collimating optic 115. A beamsplitter 118 then directs the beamlets 110 to the array of optical sensors 114 which respond with resonant reflection signals 120 that pass back through the beamsplitter 118 towards the receive system 103. It should be noted that the black arrows shown in FIG. 1 emanating from the optical sensors 114 indicate the central ray of the geometrical reflection from each sensor region and not the individual resonant responses.

The aforementioned beamlet conditioning lens(es) 106 is/are chosen to simultaneously focus all of the beamlets 110 onto a plane of the optical sensors 114 (e.g., waveguide grating sensors 114). In one embodiment, the beamlet conditioning lens 106 is a spherical lens 105 which produces a spot illumination at each optical sensor 114 in the 2-D array/microplate 116 (see FIG. 5A). In another embodiment, the beamlet conditioning lenses 106 include a spherical lens 105 and a cylindrical lens 107 which produce a line (anamorphic) illumination at each optical sensor 114 in the 2-D array/microplate 116 (see FIGS. 1, 4 and 5B). A more detailed discussion about the different beamlet conditioning lens(es) 106 that can be used is provided below with respect to FIGS. 5A and 5B.

As shown in FIG. 1, the receive system 103 includes a plano-convex object lens 122 (positive input lens 122) that receives the resonant reflection signals 120 from the beamsplitter 118 and directs the resonant reflection signals 120 to a positive ocular lens 124 (e.g., a plano-convex lens 124, image lens 124). The lenses 122 and 124 are positioned so as to form a Keplerian beam expander 126. In addition, the object lens 122 can focus the resonant reflection signals 120 through an analyzer 128 (e.g., 1"×1" analyzer 128) which may be oriented at 90° to the polarizer 108. The analyzer 128 eliminates reflections from the optical components 112, 115, and 118 that lie after the polarizer in the optical path and prior to the 2-D sensor array/microplate 116. The object lens 124 then collimates the central rays from each response beamlet 120 and adjusts the angular responses 120 so that each response 120 spans a unique region at the camera 132 (e.g., CCD camera 132) without overlapping other responses 120. A bandpass filter 134 can also be placed in front of the CCD camera 132 to reject stray environmental light.

Figure 2:
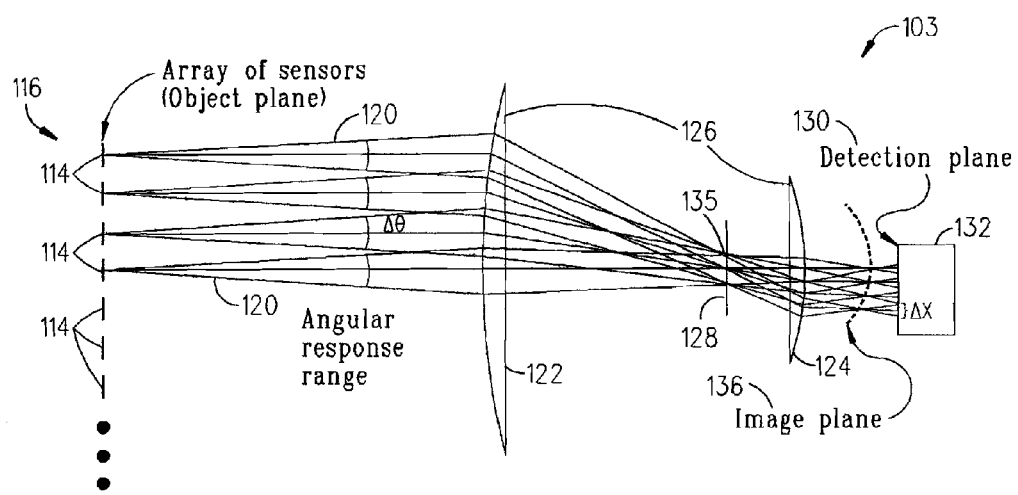
FIG. 2 is an exemplary plan view ray-trace diagram of the receive side in the optical interrogation system shown in FIG. 1.

Referring to FIG. 2, there is shown an exemplary plan view ray-trace diagram associated with the receive side 103 in the optical interrogation system 100. For clarity, the bandpass filter 134 is not shown. As discussed above, the receive side 103 includes the Keplerian beam expander 126 which is placed such that the range of possible angular responses $\Delta\theta$ from each sensor 114 is mapped onto unique sensing regions $\Delta X$ on the detection plane 130 of the CCD camera 132. The analyzer 128 is placed at a focal plane 135 of the object lens 122. The placement of the analyzer at the focal plane of the object lens 122 allows the smallest possible analyzer 128 to be used. Alternatively, other types of beam expanders may be used, such as a Galilean beam expander, although the dimensions of the analyzer 128 may need to be increased to allow passage of all of the responses 120 through the analyzer 128. Because simple plano-convex optics are used, the final image plane 136 of the two lenses 122 and 124 is a curved surface. The detection plane 130 of the CCD camera 132 is located beyond the image plane 136 at a position where the response beamlets 120 can be measured on distinct regions $\Delta X$ of the CCD camera 132.

The optical interrogation system 100 has been tested under certain conditions where the angular response beamlets 120 emanating from a numerous, 2-D array, of sensors 114 were measured sensitively and simultaneously by a large area 2-D CCD camera 132 that was placed at some distance from the array of sensors 114. The conditions were as follows:

1) The number of sensors 114 in the 2-D array which emanate an angular response was moderate (e.g. 96-well microplate 116).
2) The spacing between those sensors 114 on the object plane of the 2-D array was sufficiently large (e.g. 4.5 mm or 9 mm).
3) The spatial extent of each focused beam 110 (source point 110) at each sensor 114 in the 2-D array was small (e.g., the width of a focused beam ≈100-200 μm).
4) The angles contained in the angular response 120 that emanated from any one sensor 114 at any one time were sufficiently small (e.g., $\sigma\xi \approx 0.1°$).
5) The possible response angle displacements $\Delta x$ at the detector 132 from each sensor 114 spanned a sufficiently small dynamic range across the detector 132 (e.g., $\Delta x$=2.8 mm) which corresponds to a small dynamic range of response angles (e.g., $\Delta\theta \approx 2.3°$).
6) The detector plane 130 was located such that the dynamic range of possible sensor responses 120 from all of the sensors 114 occupied distinct regions on the large area 2-D array detector 132.

Figure 3:
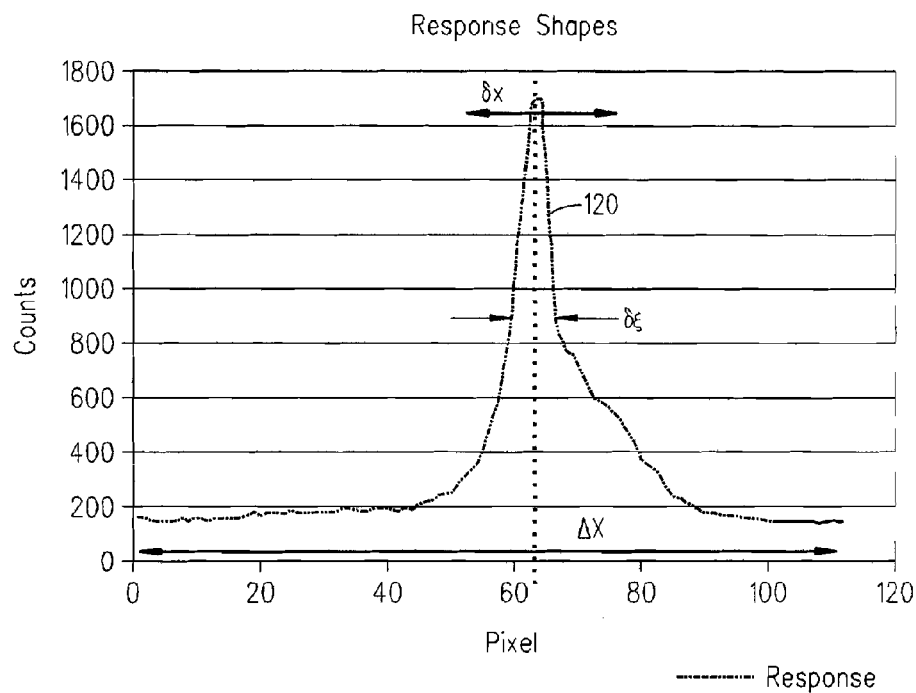
FIG. 3 is a graph that shows the angular response from a grating coupled waveguide sensor that was obtained using an optical interrogation system like the one shown in FIG. 1.

After satisfying these conditions, a telecentric ray-trace analysis could be used to accurately depict the independent and simultaneous optical responses 120 from each of the sensors 114 in the array 116 as shown in FIG. 2. FIG. 3 is a graph that shows the angular response 120 from one waveguide grating sensor 114 that was obtained under the above six listed conditions. As can be seen, the change in the response angle of the received beamlet 120 from the surface grating waveguide sensor 114 can be detected as a response shift $\delta x$ on the detector 132. The full-width-at-half-maximum $\delta\xi$ of the response beamlet 120 at the detector plane 130 was very small ($\delta\xi$=0.2 mm, 8 pixels), which corresponds to an angular response width from the sensor 114 of approximately 0.16°. The total detectable dynamic range for the sensor response 120 was a subset of pixels spanning $\Delta X$ at the detector 134. In this example, a width of $\Delta X$=112 pixels (approximately 2.8 mm) was available to measure the angular response 120 from the associated sensor 114. The $\Delta X$ width relates to the angular dynamic range $\Delta\theta$ of each beamlet 120 at the detector plane 130 and in this example is approximately 2.3° (see FIG. 2).

Figure 4:
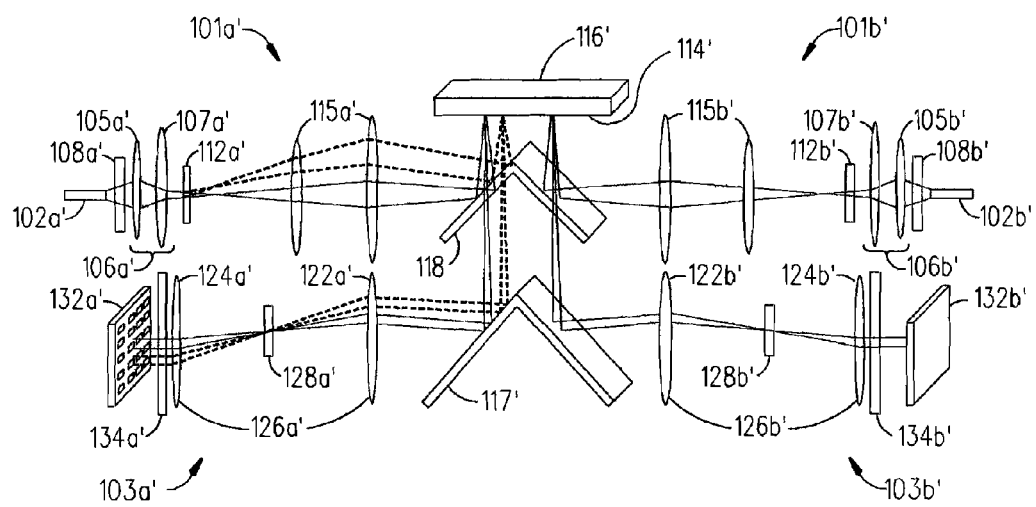
FIG. 4 is a block diagram of an optical interrogation system that has two sets of launch and receive systems which enables it to interrogate a 96-well sensor microplate using smaller diameter optical components in accordance with another embodiment of the present invention.

It should be noted that when 96 sensors 114 are arranged in a standard 96-well microplate 116, the dimensions of the sensor plane would be approximately 70 mm×100 mm and have a diagonal of 122 mm (≈5 inches). An examination of FIG. 2 shows that if a bulk optical system 100 was used to measure sensor responses from 96 sensors 114 arranged on a 96-well microplate 116 (or other microplate formats), then some of the optical components like the auto-collimating lens 115 and the positive input lens 122 shown in FIG. 1 would need to be approximately 6 inches in diameter. Because, both the cost and optical aberrations increase with the diameter of the optical components, it may be advantageous to divide the optical interrogation system 100 into two (or more) sections and dedicate two (or more) launch systems 101 and two (or more) receive systems 103 to measure the microplate 116. An example of this configuration of an optical interrogation system 100' is shown in FIG. 4 where two representative optical paths and the angular extent of each reflected response are illustrated schematically by solid and dashed lines.

As shown, the optical interrogation system 100' interrogates a full 96 well microplate 116 by using two launch systems 101a' and 101b' and two receive systems 103a' and 103b'. In this example, the optical interrogation system 100' has the following components:
laser/fiber 102a' and 102b'
polarizer 108a' and 108b'
spherical lens 105a' and 105b'
cylindrical lens 107a' and 107b'
diffractive optic 112a' and 112b'
auto-collimating lens pair 115a' and 115b'
50-50 45° beamsplitter 118a'
96-well microplate 116'
mirror 117'
focusing lens (positive input lens) 122a' and 122b'
analyzer 128a' and 128b'
magnification lens (positive objective lens) 124a' and 124b'
bandpass filter 134a' and 134b'
CCD camera 132a' and 132b'

As can be seen, the optical interrogation system 100' has a different configuration than the one shown in FIG. 1. For example, the optical interrogation system 100' has polarizers 108a' and 108b' that are located between the lasers 102a' and 102b' and the spherical lens 105a' and 105b'. This was done to show that there can be different types of components and different configurations of components that can be used in an optical interrogation system and still be considered within the scope of the present invention.

This configuration of the optical interrogation system 100' effectively decreases the area on the 96-well microplate 116 to be measured by each set of launch/receive systems to 50 mm×70 mm (86 mm diagonal, ≈3.4 inches), and allows the use of 4 or 5 inch diameter optics 115a', 115b', 122a', and 122b' (for example). In addition, the dividing of the optical interrogation system 100' into two sections one for each half of the array of sensors 114' allows the number of sensor responses 120 that need to be detected at each camera 132a' and 132$b'$ to be decreased by ½. As such, this allows each sensor measurement response region ΔX at the detector plane 130$a'$ and 130$b'$ to be increased correspondingly.

In another embodiment, the optical interrogation system 100 and 100' of the present invention can be used in conjunction with other Corning Inc. inventions that have been disclosed in the following U.S. Patent Applications:

U.S. patent application Ser. No. 10/993,565, filed Nov. 18, 2004 and entitled "System and Method for Self-Referencing a Sensor in a Micron-Sized Deep Flow Chamber".

U.S. patent application Ser. No. 11/027,509, filed Dec. 29, 2004 and entitled "Method for Creating a Reference Region and a Sample Region on a Sensor and the Resulting Sensor".

The contents of these applications are incorporated by reference herein.

These inventions have shown that a self-referencing sensor which is located in the well of a microplate can be interrogated in a manner to eliminate environmental effects such as temperature and to minimize instrumental effects such as thermal displacement of optical components and laser wavelength drift. Basically, these self-referencing sensors were made such that different binding, kinetic, or near-surface transport events can occur on their top surfaces in spatially resolvable locations. In particular, one self-referencing sensor was located under a micron-sized deep flow channel that had parallel flows of fluids (see U.S. patent application Ser. No. 10/993,565). And, one self-referencing sensor had binding and non-binding regions located on its top surface (see U.S. patent application Ser. No. 11/027, 509).

Figure 5A:
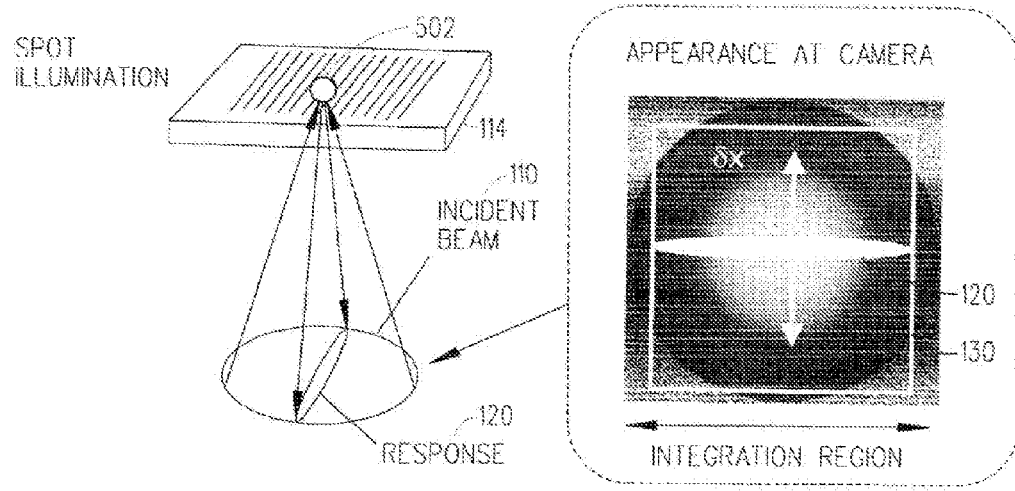
FIGS. 5A and 5B illustrate two different ways that the optical interrogation systems shown in FIGS. 1 and 4 can illuminate a 2-D array of grating coupled waveguide sensors.
Figure 5B:
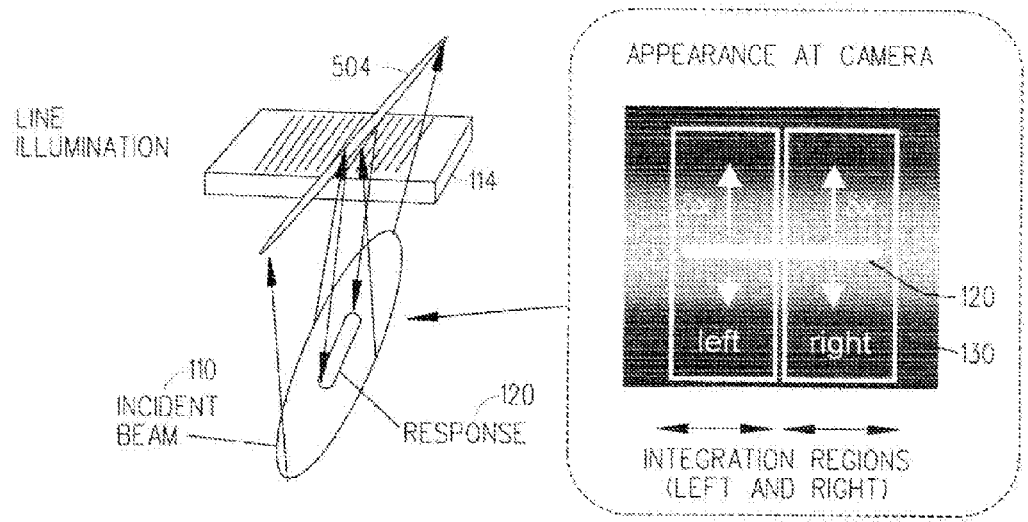

The aforementioned optical interrogation systems 100 and 100' which have a line (anamorphic) launch end 101, 101$a'$ and 101$b'$ can be used to angularly interrogate these and other types of self-referencing sensors 114 (see FIGS. 5B). Again, the anamorphic launch end 101, 101$a'$ and 101$b'$ contains beamlet conditioning lenses 106, 106$a'$ and 106$b'$ which include both the spherical lens 105, 105$a'$ and 105$b'$ and the cylindrical lens 107, 107$a'$ and 107$b'$ (see FIGS. 1 and 4). In addition, the optical interrogation system 100 and 100' would have a CCD camera 134, 134$a'$ and 134$b'$ which can spatially resolve the angular response 120 from locations across the width of an array of self-referencing sensors 114. In this way, regions of interest (ROIs) can be defined across each of the sensor's responses 120 as observed at the detector plane 130, 130$a'$ and 130$b'$. And, these ROIs correspond to specific locations across the width of the self-referencing sensor 114. The responses 120 from each region on the top surface of the self-referencing sensor 114 can then be analyzed separately and subtracted from one another (referenced), if desired. This results in an increase in the achievable sensitivity, because the environment within a well of a microplate 116 is very uniform thermally and because the optical paths of the rays in the line illumination are nearly identical. Hence, this within well referencing technique can eliminate the need for costly environmental controls, low thermal expansion materials, and laser stabilization methods.

To implement this self-referencing technique, the optical interrogation system 100 and 100' and in particular the launch system 101, 101$a'$ and 101$b$40 would have appropriately sized beamlet conditioning lenses 106, 106$a'$ and 106$b'$—cylindrical lens 105, 105$a'$ and 105$b'$ and spherical lens 107, 107$a'$ and 107$b'$ (see FIGS. 1 and 4). These beamlet conditioning optics 106, 106$a'$ and 106$b'$ are chosen such that a line illumination is focused at the plane of the sensor 114 (see FIG. 5B). Since, the diffractive optic 112, 112$a'$ and 112$b'$ makes "copies" of the beam 110 that passes through it, the optical interrogation system 100 and 100' can be designed to faithfully reproduce a low numerical aperture line illumination at locations on all of the sensors 114 in the 2-D array simultaneously.

Referring to FIGS. 5A and 5B, there are illustrated two different ways that the optical interrogation system 100 and 100' can illuminate the grating waveguide sensors 114. As shown in FIG. 5A, the incident light 110 can be focused to a point/spot 502 at the sensor 114 by using one or more spherical beamlet conditioning lenses 105, 105$a'$ and 105$b'$. The photograph in FIG. 5A shows the angular response 120 of the sensor 114 at the detector plane 130. In this case, the angular response 120 from the sensor 114 is the reflection of a small range of angles present in the incident beam 110. As can be seen in the photograph, the sensor's angular response 120 to the index of refraction at its surface displaces the reflection by δx. This angular response 120 is analyzed by a processor (not shown) which selects a region of interest (ROI, white box) and then integrates along the horizontal direction to produce an integrated angular response curve like the one shown in FIG. 3.

As shown in FIG. 5B, the incident light 110 can be focused to a line 504 across the sensor 114 by using an anamorphic launch system 101 and 101' that includes both spherical and cylindrical optics 105, 105$a'$, 105$b'$, 106, 106$a'$ and 106$b'$ (see FIGS. 1 and 3). The choice of appropriate cylindrical and spherical optics 105, 105$a'$, 105$b'$, 106, 106$a'$ and 106$b'$ enables the preservation of the spatial information of the optical response 120 from across the width of the sensor 114 as seen at the CCD camera 132, 132$a'$ and 132$b'$. In this case, multiple ROIs (e.g. left and right) may be defined by a processor (not shown) and analyzed independently across the width of each sensor's measured response 120 (see photograph in FIG. 5B). Then, these ROIs can be subsequently referenced against one another. This makes it possible to implement simultaneous assays from 2-D arrays of self-referencing sensors 114 using the aforementioned within-well self-referencing techniques.

Figure 6:
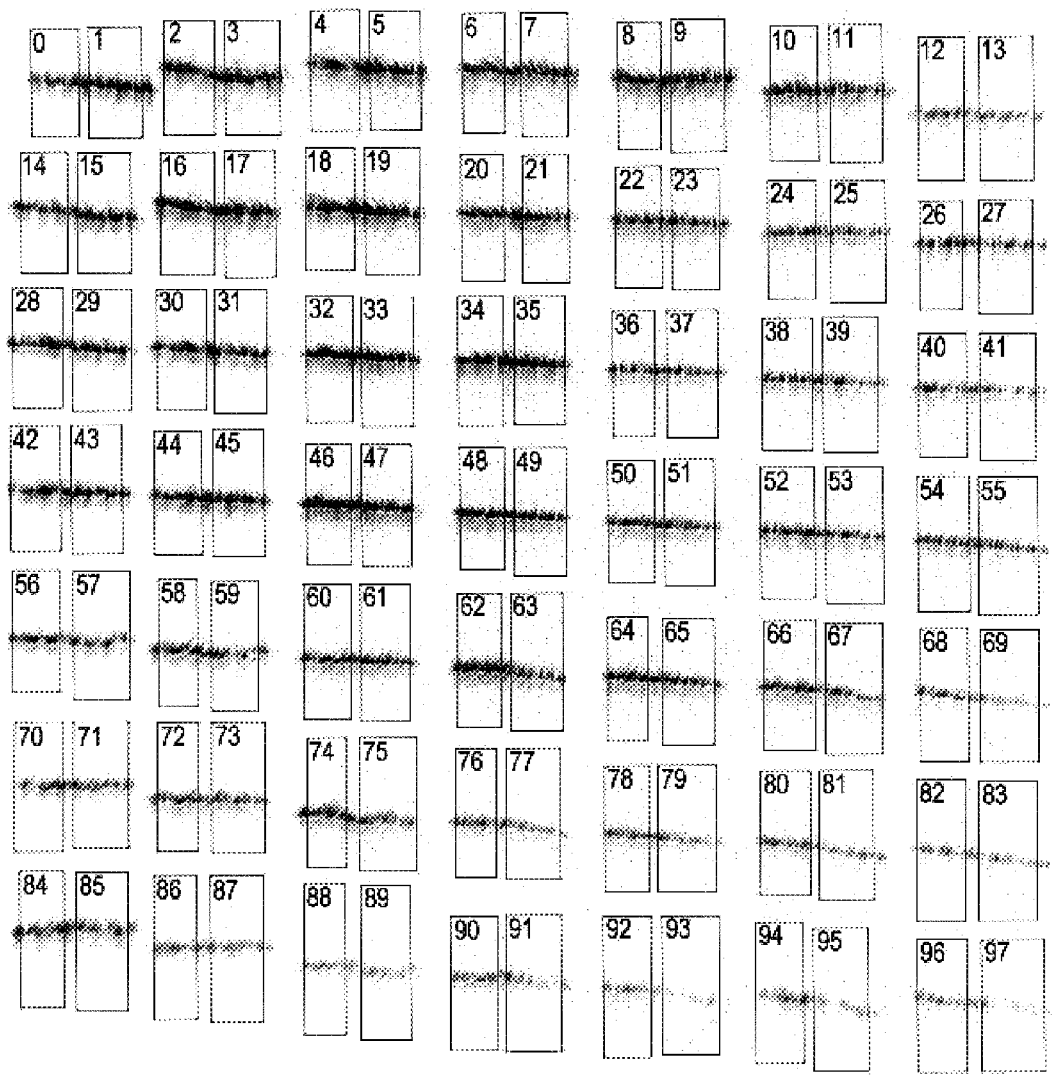
FIG. 6 is a negative image of optical responses that were generated by a CCD camera while testing the optical interrogation system shown in FIG. 1.

Referring to FIG. 6, there is shown a negative image of optical responses 120 generated by a CCD camera that was obtained after inserting a 7×7 diffractive optic 112 into the optical interrogation system 100 shown in FIG. 1 which simultaneously produced line illuminations across the width of 49 sensors 114. The negative of the actual image of the optical responses 120 is shown to enhance clarity. In this experiment, the surface grating waveguide sensors 114 were spaced at intervals of 9 mm in a standard 96-well microplate 116. The detector 132 was a 1024×1024 pixel camera with a 1"×1" width. Using software, 49 pairs of regions of interest (ROIs), each spanning an area of approximately 65×125 pixels, were defined for analysis. Each region included the responses 120 from the left (odd numbers) or right half (even numbers) of one self-referencing sensor 114. These 98 ROIs were separately integrated using software to produce the angular responses for those ROIs. The left and right half responses from each well can be subtracted from one another (referenced) when appropriate to remove environmental effects and other undesirable effects. A similar result was obtained in another experiment in which a spot on 49 sensors 114 were illuminated; in this case the ROIs were defined to include the entire width of each response region at the camera 132 (see FIG. 5A).

Figure 7:
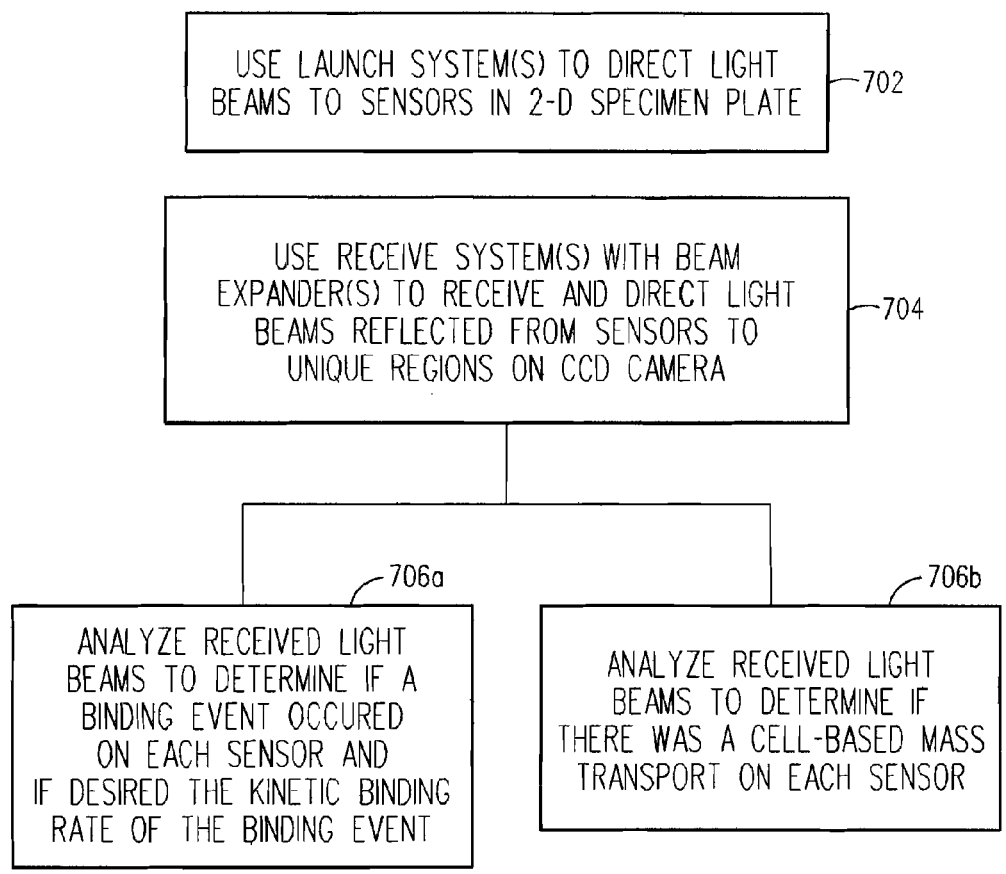
FIG. 7 is a flowchart that illustrates the basic steps of a method for interrogating an array of sensors located in a two-dimensional specimen plate in accordance with the present invention.

Referring to FIG. 7, there is shown a flowchart that illustrates the basic steps of a method 700 for interrogating an array of sensors 114 in a two-dimensional specimen plate 116. Beginning at step 702, one or more launch systems 101 are used to direct an array of light beams 110 towards the array of sensors 114 in the two-dimensional specimen plate 116. At step 704, one or more receive systems 103 each of which has a beam expander 126 (which may be a Keplerian beam expander 126) therein is used to receive the array of the light beams 120 reflected from the array of sensors 114 and direct each received light beam 120 to a unique region on a detection plane 130 in one or more cameras 132. At step 706a, a processor (not shown) is used to analyze each received light beam 120 to determine whether or not a biomolecular binding event occurred in a specimen, or to determine the rate of binding in a specimen located on one of the sensors 114. Alternatively, at step 706b, a processor (not shown) is used to analyze each received light beam 120 to determine whether or not there was a cell-based mass transport in a specimen located on one of the sensors 114.

Following are some advantages and uses of the optical interrogation system 100 and 100' and method 700 of the present invention:

The optical interrogation system 100 and 100' enables the simultaneous high speed and high sensitivity HTS screening of many sensors 114 in a 2-D array. In particular, the optical interrogation system 100 and 100' can be used to characterize the kinetic binding response, concentration dependence, and near surface mass transport on sensors 114. In addition, the optical interrogation system 100 and 100' can been used to develop cell-based assays that can be used with or without in-well referencing techniques using LID technology with waveguide grating sensors 114.

The optical interrogation system 100 and 100' allows multiple sensor responses to be measured at the same time using a large area CCD camera. The present invention also demonstrates that it is possible to use an anamorphic optical launch technique in combination with a diffractive optic to generate line illumination across a 2D array of sensors 114 and to separately resolve the optical responses 120 from across the width of every sensor 114 in the array simultaneously. This enables sensor self-referencing to be used while interrogating the 2-D array of sensors 114.

The present invention enables the simultaneous measurement of the angular responses 120 from a 2-D array of waveguide grating sensors 114 by measuring the displacements of those angular responses 120 with a 2-D CCD camera 132 that is located at some distance from the sensor array 114. This is possible, if the microplate 116 (or sensor array 114) is sufficiently flat and the angular responses 120 of all of the sensors 114 lie within a sufficiently narrow range. Then, a telecentric beam condensing receive system 103 may be used together with a large area camera detector 132 in accordance with the present invention to enable the simultaneous interrogation of large number of sensors 114. The beam condensing receive optics 103 serve to minimize the spatial extent of the array of sensors' responses 120 and to magnify the angular responses 120 at the detection plane 130 (e.g. a camera 132). If the angular dynamic range is sufficiently small and the camera detector 132 is of a sufficiently large area, then it is possible to map the angular response 120 from each sensor 114 onto unique regions on the detector plane 130, thus enabling simultaneous angular detection of a 2-D array containing many sensors.

The optical interrogation system 100 and 100' is also capable of simultaneously obtaining within-well referencing data for a 2D array of sensors 114 by allowing the simultaneous spatial resolution of the angular responses 120 from different locations across each of the sensors 114. This is accomplished by the use of a cylindrical optic 105 and spherical optic 107 (or equivalently a line generating optic) as the beamlet conditioning lenses 106. This simultaneous within-well referencing of each sensor 114 has a great utility for referencing out environmental and laser wavelength drift effects and thus can increase the achievable sensitivity for detecting small index shifts from a 2-D array of sensors 114.

The optical interrogation system 100 and 100' enables the simultaneous measurement of the angular responses 120 from a 2-D array of waveguide grating sensors 114 by measuring those angular responses 120 as displacements in the plane of a 2-D CCD camera 132, which is located at some distance from the sensor array. Some of the advantages associated with this invention are that it:
  (i) contains a small number of components,
  (ii) has a higher degree of tolerance to response angle variations, sensor plane flatness, and sensor plane angular variations than other methods of measurement,
  (iii) contains no moving or scanning parts, and
  (iv) can simultaneously measure and process the responses of a 96 microplate of waveguide grating sensors in less than 3 seconds.

The optical interrogation systems 100 and 100' could be applied in the following applications (for example):
  Grating and non-grating based sensors.
  Fluorescence, fluorescence spectroscopy, fluorescence lifetime spectroscopy, scattering, emission, reflection, infrared and ultra-violet absorption spectroscopy, Fourier transform infrared absorption (FTIR) spectroscopy, Raman spectroscopy, reflection spectroscopy, and surface plasmon resonance spectroscopy.

The preferred sensor 114 described herein is a grating-coupled waveguide sensor 114. The following documents disclose details about the structure and the functionality of this type of sensor 114:
  (1) U.S. Pat. No. 4,815,843 entitled "Optical Sensor for Selective Detection of Substances and/or for the Detection of Refractive Index Changes in Gaseous, Liquid, Solid and Porous Samples".
  (2) K. Tiefenthaler et al. "Integrated Optical Switches and Gas Sensors" Opt. Lett. 10, No. 4, April 1984, pp. 137-139.

It should also be understood that the present invention can also use launch systems or various combinations of those launch systems described in U.S. patent application Ser. Nos. 10/602,304 and 11/019,439, where the need for those combinations would be readily apparent to persons familiar with optical technology.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:
1. An optical interrogation system comprising:
  a launch system for directing an array of light beams towards an array of sensors in a two-dimensional specimen plate; and
  a receive system including:
    a beam expander; and
    a detector;

said beam expander for receiving the array of said light beams reflected from the array of sensors, and for reducing the dimension of the array of said light beams and directing each received light beam to a unique region on a detection plane in said detector, wherein said detector is located past an image plane associated with said beam expander for the purpose of measuring response angles in the array of said light beams reflected from the array of sensors in the two-dimensional specimen plate.

2. The optical interrogation system of claim 1, wherein said beam expander is a Kieplerian beam expander that includes:
a plano-convex object lens; and
a positive ocular lens.

3. The optical interrogation system of claim 1, wherein said receive system further includes:
an analyzer for substantially eliminating reflections within the received light beams that are caused by optical components in said launch system.

4. The optical interrogation system of claim 1, wherein said receive system further includes:
a bandpass filter for substantially rejecting stray light that can be detected by said detector.

5. The optical interrogation system of claim 1, wherein said launch system further includes a spherical lens which causes each light beam to illuminate a spot on each sensor in the two-dimensional specimen plate.

6. The optical interrogation system of claim 1, wherein said launch system further includes (a) one or more spherical lenses and one or more cylindrical lenses or (b) one or more line generating lenses which have the effect of causing each light beam to illuminate a line across each sensor in the two-dimensional specimen plate.

7. The optical interrogation system of claim 6, wherein said receive system detects a plurality of optical responses in each received light beam from the line across the illuminated region of each sensor in the two-dimensional specimen plate.

8. The optical interrogation system of claim 7, wherein said receive system spatially divides each received optical response into at least two separate responses, so as to generate separate signal and reference responses that can be subsequently used for self referencing.

9. The optical interrogation system of claim 8, where the signal and reference responses are differenced to produce a referenced response.

10. The optical interrogation system of claim 1, further comprising a processor for analyzing one of the received light beams to determine whether or not a biomolecular binding event occurred, or to determine the rate of binding in a specimen located on one of the sensors in the two-dimensional specimen plate.

11. The optical interrogation system of claim 1, further comprising a processor for analyzing one of the received light beams to determine whether or not there was a cell-based mass transport in a specimen located on one of the sensors in the two-dimensional specimen plate.

12. A receive system comprising:
an object lens;
an image lens; and
a detector;
wherein said object lens receives an array of light beams reflected from a plurality of sensors;
wherein said image lens directs each received light beam to a unique region on a detection plane in said detector; and
wherein said detector is located past an image plane associated with said object and image lenses for the purpose of measuring the response angles from said plurality of sensors.

13. The receive system of claim 12, further comprising an analyzer located between said object lens and said image lens.

14. The receive system of claim 12, further comprising a bandpass filter located between said image lens and said detector.

15. A method for interrogating an array of sensors in a two-dimensional specimen plate, said method comprising the steps of:
using a launch system to direct an array of light beams towards the array of sensors in the two-dimensional specimen plate; and
using a receive system that has a beam expander to receive the array of the light beams reflected from the array of sensors and direct each received light beam to a unique region on a detection plane in a detector, wherein said detector is located past an image plane associated with said beam expander for the purpose of measuring response angles in the array of said light beams reflected from the array of sensors in the two-dimensional specimen plate.

16. The method of claim 15, wherein said detector has a smaller area than the array of sensors.

17. The method of claim 15, further comprising the step of analyzing each received light beam to determine whether or not a biomolecular binding event occurred, or to determine the rate of binding in a specimen located on each sensor.

18. The method of claim 15, further comprising the step of analyzing each received light beam to determine whether or not there was a cell-based mass transport in a specimen located on each sensor.

19. The method of claim 15, further comprising the step of using said launch system which has a spherical lens that causes each light beam to illuminate a spot on each sensor in the two-dimensional specimen plate.

20. The method of claim 15, further comprising the step of using said launch system which has a spherical lens and a cylindrical lens or a line generating lens that causes each light beam to illuminate a line across each sensor in the two-dimensional specimen plate.

21. The method of claim 20, further comprising the step of using said receive system to determine a plurality of optical responses in each received light beam that was illuminated across the line in each sensor in the two-dimensional specimen plate.

22. The method of claim 20, further comprising the step of using said receive system to analyze the optical responses in each received light beam to self-reference each sensor in the two-dimensional specimen plate.

23. The method of claim 15, wherein each sensor has a binding region and a non-binding region.

24. The method of claim 15, wherein each sensor is a grating-coupled waveguide sensor.

25. The method of claim 15, wherein each sensor is associated with a micron-sized deep flow channel.

26. The method of claim 25, wherein each sensor has portions that are associated with parallel flows of fluids in contact with each other in a micron-sized deep flow chamber.

27. The method of claim 15, wherein said two-dimensional specimen plate is a microplate.

28. An optical interrogation system comprising:
a launch system for directing an array of light beams towards an array of sensors in a two-dimensional specimen plate; and
a receive system including:
  a beam expander; and
  a detector;
  said beam expander for receiving the array of said light beams reflected from the array of sensors, and for reducing the dimension of the array of said light beams and directing each received light beam to a unique region on a detection plane in said detector; and
  said beam expander is a Keplerian beam expander that includes:
    a plano-convex object lens; and
    a positive ocular lens.

29. An optical interrogation system comprising:
a launch system for directing an array of light beams towards an array of sensors in a two-dimensional specimen plate; and
a receive system including:
  a beam expander; and
  a detector;
  said beam expander for receiving the array of said light beams reflected from the array of sensors, and for reducing the dimension of the array of said light beams and directing each received light beam to a unique region on a detection plane in said detector; and
said launch system further includes (a) one or more spherical lenses and one or more cylindrical lenses or (b) one or more line generating lenses which have the effect of causing each light beam to illuminate a line across each sensor in the two-dimensional specimen plate.

30. The optical interrogation system of claim 29, wherein said receive system detects a plurality of optical responses in each received light beam from the line across the illuminated region of each sensor in the two-dimensional specimen plate.

31. The optical interrogation system of claim 30, wherein said receive system spatially divides each received optical response into at least two separate responses, so as to generate separate signal and reference responses that can be subsequently used for self referencing.

32. The optical interrogation system of claim 31, where the signal and reference responses are differenced to produce a referenced response.

33. A method for interrogating an array of sensors in a two-dimensional specimen plate, said method comprising the steps of:
using a launch system to direct an array of light beams towards the array of sensors in the two-dimensional specimen plate, wherein said launch system has a spherical lens and a cylindrical lens or a line generating lens that causes each light beam to illuminate a line across each sensor in the two-dimensional specimen plate; and
using a receive system that has a beam expander to receive the array of the light beams reflected from the array of sensors and direct each received light beam to a unique region on a detection plane in a detector.

34. The method of claim 33, further comprising the step of using said receive system to determine a plurality of optical responses in each received light beam that was illuminated across the line in each sensor in the two-dimensional specimen plate.

35. The method of claim 34, further comprising the step of using said receive system to analyze the optical responses in each received light beam to self-reference each sensor in the two-dimensional specimen plate.

36. The optical interrogation system of claim 1, wherein said beam expander is a Galilean beam expander.

* * * * *